United States Patent [19]

Reiners et al.

[11] Patent Number: 4,870,202
[45] Date of Patent: Sep. 26, 1989

[54] (METH)-ACRYLIC ACID DERIVATIVES OF TRIISOCYANATES AND THEIR USE

[75] Inventors: Jürgen Reiners, Leverkusen; Carlhans Süling, Odenthal; Wolfgang Podszun; Jens Winkel, both of Cologne, all of Fed. Rep. of Germany

[73] Assignee: Bayer Aktiengesellschaft, Leverkusen, Fed. Rep. of Germany

[21] Appl. No.: 131,152

[22] Filed: Dec. 10, 1987

[30] Foreign Application Priority Data

Dec. 18, 1986 [DE] Fed. Rep. of Germany ....... 3643216

[51] Int. Cl.$^4$ .............................................. C07C 125/06
[52] U.S. Cl. ................................................... 560/158
[58] Field of Search .......................................... 560/158

[56] References Cited

U.S. PATENT DOCUMENTS 4,279,833  7/1981  Culbertson et al. ................ 560/158

FOREIGN PATENT DOCUMENTS 2308036  10/1973  Fed. Rep. of Germany .
3117006   1/1982  Fed. Rep. of Germany .
3643216   6/1988  Fed. Rep. of Germany ...... 560/158
2079297   1/1982  United Kingdom .

Primary Examiner—Joseph L. Schofer
Assistant Examiner—N. Sarofim
Attorney, Agent, or Firm—Sprung Horn Kramer & Woods

[57] ABSTRACT

New (meth)acrylic acid derivatives of triisocyanates can be prepared by reaction of aliphatic triisocyanates with hydroxyalkyl (meth)acrylates. The new compounds can be used as monomers in dental materials.

6 Claims, No Drawings

(METH)-ACRYLIC ACID DERIVATIVES OF TRIISOCYANATES AND THEIR USE

The invention relates to new acrylic acid and methacrylic acid derivatives of aliphatic triisocyanates, called (meth)-acrylic acid derivatives below, and to their preparation. The new compounds can be employed as monomers for use in the dental field.

Polyurethane-polyacrylates which can be used as adhesives are known from U.S. Pat. No. 3,425,988.

Japanese Pat. No. 81/127,609 likewise describes polyurethane-polyacrylates which are used in plastics or as dyestuff components.

Dental filling materials which contain, for example, bis-(1,3-dimethacryloyloxy-2-propanetriyl) N,N'-hexamethylenedicarbamate are known from U.S. Pat. No. 4,394,494. These compounds exhibit unsatisfactory abrasion properties.

New (meth)acrylic acid derivatives of aliphatic triisocyanates of the formula (I)

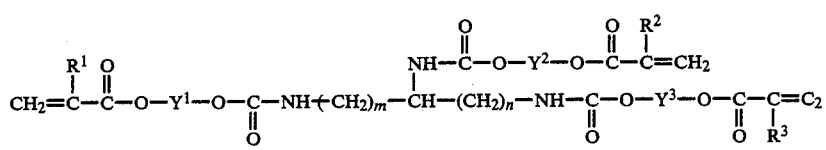

in which
R$^1$, R$^2$ and R$^3$ are identical of different and denote hydrogen or methyl,
m and n independently of one another represent a number from 2 to 6 and
Y$^1$ to Y$^3$ are identical or different and denote divalent straight-chain or branched aliphatic hydrocarbon radicals which have 2 to 15 carbon atoms, can optionally contain 1 to 3 oxygen bridges and can optionally be substituted by 1 to 4 additional (meth)acryloyloxy radicals,
have been found.

The (meth)acrylic acid derivatives can be in the form of pure isomers or isomer mixtures. Isomer mixtures can be employed for the use according to the invention of the (meth)acrylic acid derivatives in dental materials.

In the context of the present invention, the substituents can in general have the following meaning.

Divalent hydrocarbon radicals Y$^1$ to Y$^3$ can denote straight-chain or branched aliphatic hydrocarbon radicals with 2 to 15 carbon atoms, preferably 2 to 10 carbon atoms The radicals Y$^1$ and Y$^3$ can optionally contain 1 to 3 oxygen bridges, preferably 1 or 2 oxygen bridges. It is also possible for the radicals Y$^1$ to Y$^3$ to be substituted by 1 to 4, preferably 1 or 2, (meth)-acryloyloxy radicals. The following radicals may be mentioned as examples:

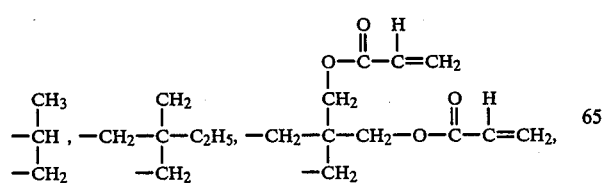

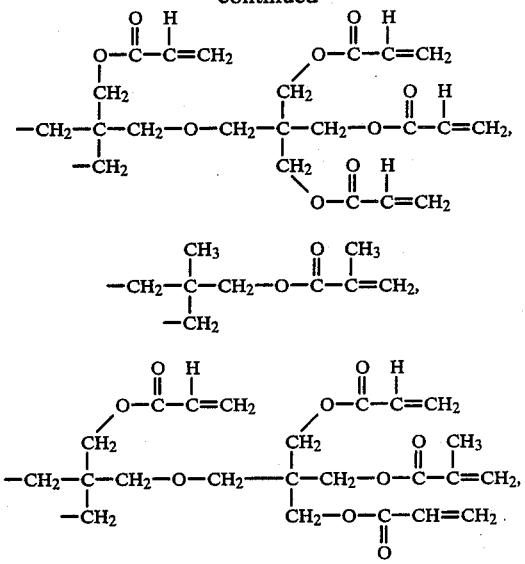

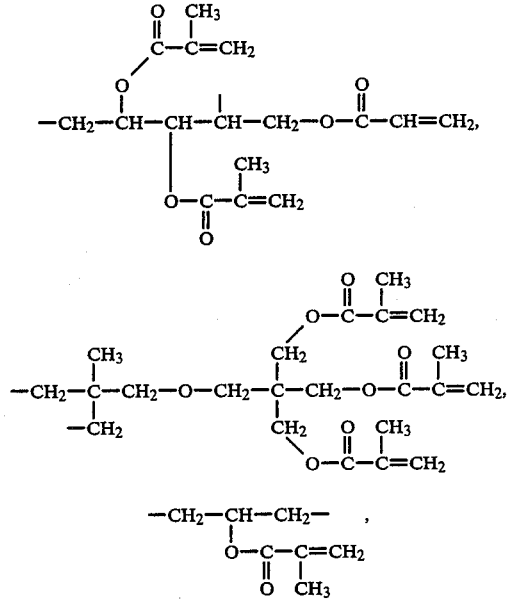

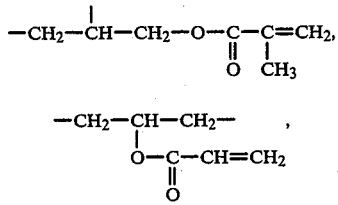

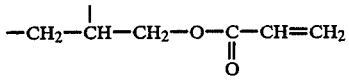

The new (meth)acrylic acid derivatives are colorless, have a low volatility and give transparent materials after polymerization.

They are particularly suitable for use for dental materials, such as dental filling compositions and coating agents. The materials thus obtained are distinguished by a surprisingly high resistance to physical and chemical stress. The hardness, abrasion resistance and breaking strength are particularly improved in comparison with customary materials used for this purpose.

Preferred (meth)-acrylic acid derivatives are those of the formula (I) wherein $R^1$ to $R^3$ are identical or different and denote hydrogen or methyl, m and n independently of one another represent a number from 2 to 6, the sum of m+n being 8 to 12, and $Y^1$ to $Y^3$ are identical or different and denote divalent straight-chain or branched aliphatic hydrocarbon radicals which have 2 to 15 carbon atoms, can optionally contain 1 to 3 oxygen bridges and can optionally be substituted by 1 or 2 additional (meth-)acryloyloxy radicals.

Particularly preferred (meth)acrylic acid derivatives of the formula (I) are those in which $R^1$ to $R^3$ are identical or different and represent hydrogen or methyl, m and n are identical or different and represent a number from 2 to 6, the sum of m+n being 9 to 11, and $Y^1$ to $Y^3$ are identical or different and denote divalent straight-chain or branched aliphatic hydrocarbon radicals which have 2 to 10 carbon atoms, can optionally contain 1 or 2 oxygen bridges and can optionally be substituted by 1 or 2 additional (meth-)acryloyloxy radicals.

The following (meth)acrylic acid ester derivatives may be mentioned as examples:

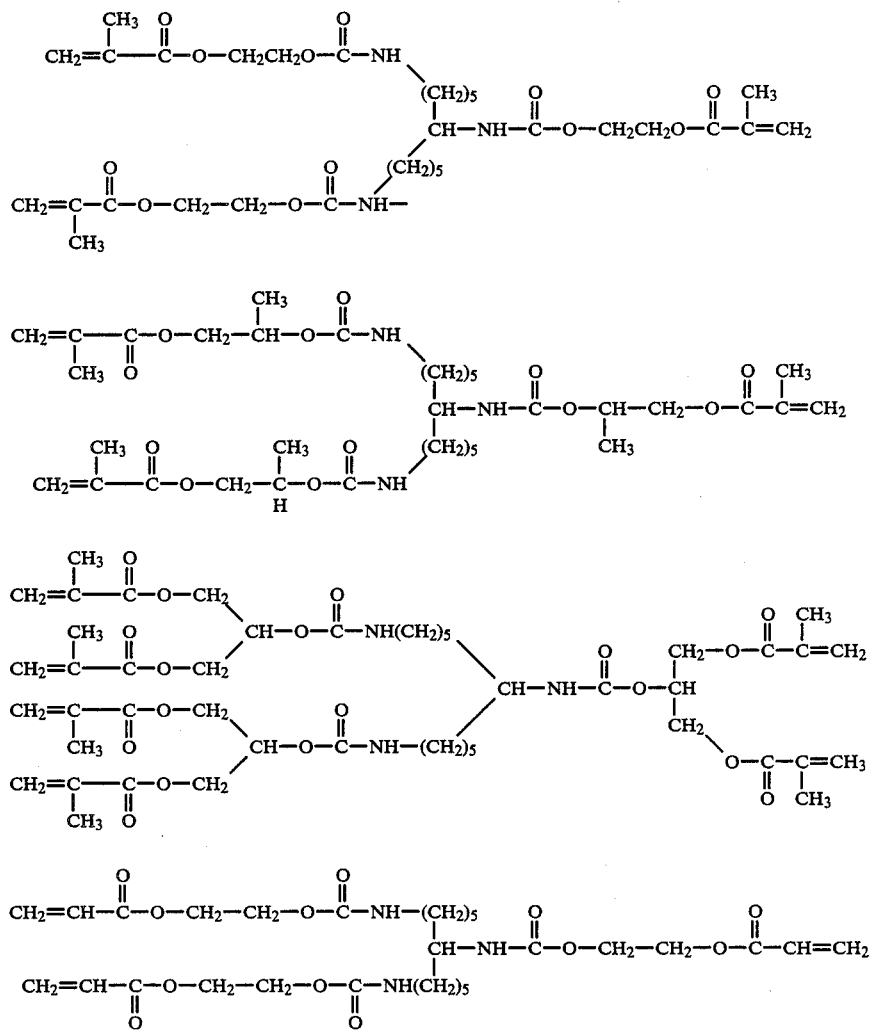

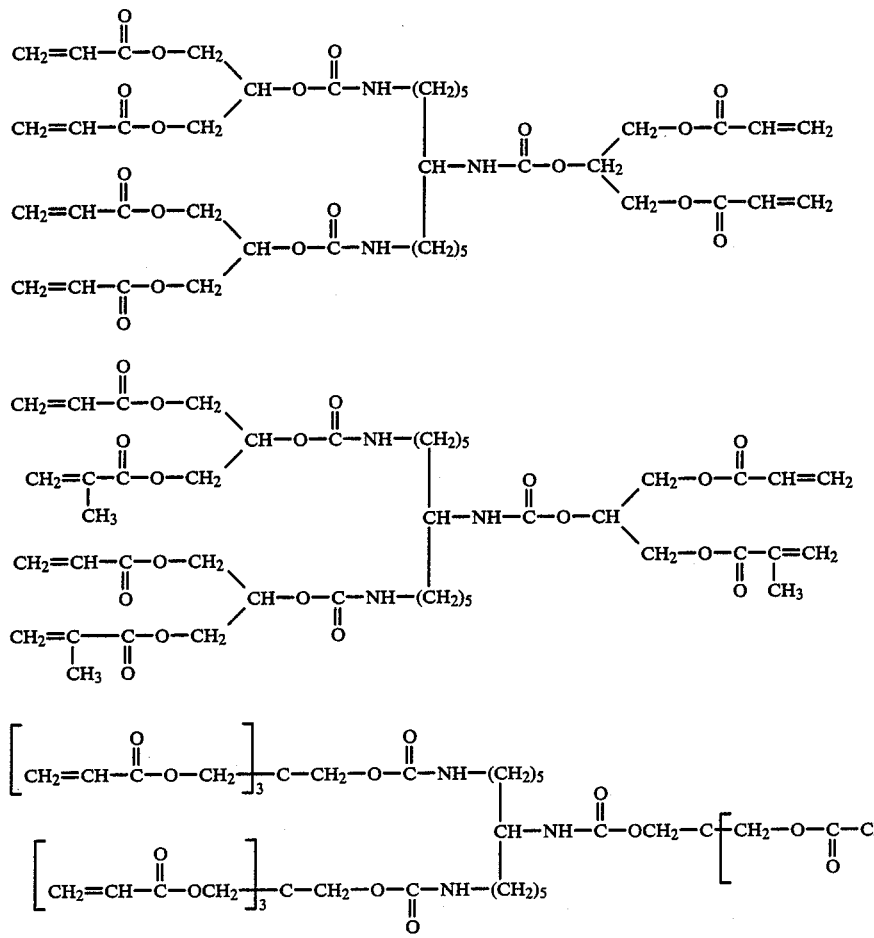

A process has also been found for the preparation of the (meth)acrylic acid derivatives according to the invention, which is characterized in that a triisocyanate of the formula (II)

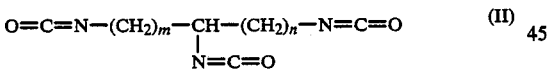

in which m and n independently of one another represent a number from 2 to 6, is reacted with a hydroxyalkyl (meth)acrylate of the formula

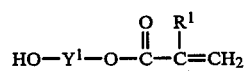 (III)

and/or

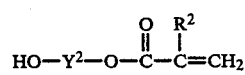 (IV)

and/or

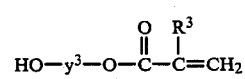 (V)

in which $R^1$, $R^2$ and $R^3$ are identical or different and denote hydrogen or methyl and $Y^1$ to $Y^3$ are identical or different and denote divalent straight-chain or branched aliphatic hydrocarbon radicals which have 2 to 15 carbon atoms, can optionally contain 1 to 3 oxygen bridges and can optionally be substituted by 1 to 4 additional (meth)acryloyloxy radicals.

Triisocyanates of the formula II are known (German Pat. No. A-2,924,149) and can be obtained by phosgenation of the corresponding triamino compounds.

Hydroxyalkyl (meth)acrylates of the formula III to V are commercially available or can be prepared in a known manner by partial esterification of the corresponding polyols.

In carrying out the process according to the invention, in general 0.9 to 1.1, preferably 1.0 to 1.05 mol of one or more hydroxyalkyl (meth)acrylates of the formulae III, IV or V or mixtures of these compounds are employed for each isocyanate group of the triisocyanate of the formula II, and the sum of all the hydroxyl equivalents for each isocyanate group of the triisocyanate of the formula (II) should be 0.9 to 1.1, preferably 1.0 to 1.05.

The process according to the invention is in general carried out in an inert solvent. Examples which may be mentioned are chloroform, tetrahydrofuran, acetone, dioxane, methylene chloride, toluene and acetonitrile. Preferred solvents are chloroform, toluene, acetone and methylene chloride.

The process according to the invention is in general carried out in the temperature range from 20° to 100° C., preferably 30° to 70° C.

The process according to the invention is in general carried out under atmospheric pressure. However, it is also possible for the process to be carried out in the pressure range from 1 to 15 bar.

The reaction according to the invention to give the urethane is preferably carried out with exclusion of water (preferably with less than 0.1% of water).

Tin-containing catalysts, such as dibutyl-tin dilaurate, tin(II) octoate or dibutyl-tin dimethoxide, are preferably used to accelerate the reaction.

It is also possible for compounds with tertiary amino groups or titanium compounds to be used as catalysts. The following catalysts may be mentioned as examples: diazabicyclo[2.2.2]octane, triethylamine, N-methylpiperidine or tetrabutoxy-titanium (Ullmann, Encyclopädie der technischen Chemie (Encyclopedia of Industrial Chemistry), volume 19, page 306 (1981)).

The catalyst is in general employed in an amount of 0.01 to 2.5% by weight, preferably 0.1 to 1.5% by weight, based on the total amount of the reactants.

The reaction to give the urethane is in general carried out in the presence of 0.01 to 0.2% by weight of a polymerization inhibitor, for example 2,6-di-tert.-butyl-4-methylphenol.

The process according to the invention can be carried out, for example, as follows:

The reactants are dissolved in the solvent and the catalyst is added, with stirring. The course of the reaction with respect to time can be monitored, for example, by measurement of the IR spectra. When reaction of the isocyanate groups is complete, the reaction products are isolated by removing the solvent. Prior purification with the aid of absorbents, for example active charcoal, bleaching earth, silica gel or aluminum oxide, is of course also possible.

The (meth)-acrylic acid derivatives of triisocyanates according to the invention can be used as monomers for polymeric materials. The polymerization can be carried out in a manner which is known per se by free radical initiation and gives polymers which have a high cross-linking density.

The (meth)-acrylic acid derivatives of triisocyanates according to the invention can be used in particular as monomers for dental materials. Examples of dental materials which may be mentioned are filling materials for teeth, coating agents for teeth and components for the production of dentures. The dental materials can contain other auxiliaries, depending on the field of use.

The dental materials according to the invention preferably contain 10 to 75% by weight, particularly preferably 30 to 70% by weight, of (meth)acrylic acid derivatives of triisocyanates based on the amount of polymerizable compounds employed.

For use as monomers for polymeric dental filling compositions or coating agents (dental lacquers) in the dental field, the (meth)-acrylic acid derivatives of triisocyanates according to the invention can be mixed with comonomers which are known per se. Thus, for example, the viscosity can be adjusted to suit the intended use. These monomer mixtures in general have a viscosity in the range from 60 to 10,000 mPa.s.

The following comonomers may be mentioned as examples: triethylene glycol dimethacrylate, tetraethylene glycol dimethacrylate, 1,12-dodecanediol dimethacrylate, 1,6-hexanediol dimethacrylate, diethylene glycol dimethacrylate, 2,2-bis[p-(2'-hydroxy-3'-methacryloyloxypropoxy)phenyl]propane and 2,2-bis[p-(2'-methacryloyloxyethoxy)phenyl]propane. Comonomers with urethane groups, for example the known reaction products of 1 mol of a diisocyanate, for example hexamethylene diisocyanate, trimethylhexamethylene diisocyanate or isophorone diisocyanate, with 2 mol of a hydroxyalkyl (meth)acrylate, for example glycerol dimethacrylate or 2-hydroxypropylacrylate, are also of advantage.

Other examples of comonomers are: trimethylolpropane tri(meth)-acrylate, bis(meth)acryloyloxyethoxymethyl)-tricyclo[5.2.1.0$^{2.2}$]decane (according to German Pat. Nos. A-2,931,925 and 2,931,926), 1,3-di((meth)acryloyloxypropyl)-1,1,3,3-tetramethyl-disiloxane and 1,3-bis(3-(meth)acryloyloxyethylcarbamoyloxypropyl)-1,1,3,3-tetramethyl-disiloxane. Comonomers which have a boiling point above 100° C. under 13 mbar are particularly preferred.

In the context of the present invention, it is also preferable to use mixtures of various (meth)-acrylic acid derivatives according to the invention.

It is also possible to use monomer mixtures which contain several comonomers.

The (meth)acrylic acid derivatives of triisocyanates according to the invention, if appropriate mixed with the monomers mentioned, can be hardened to cross-linked polymers by methods which are known per se (G. M. Brauer, H. Argentar, Am. Chem. Soc., Symp. Ser. 212, pages 359–371 (1983)). A system of a peroxidic compound and a reducing agent, for example based on tertiary aromatic amines, is suitable for so-called redox polymerization. Examples of peroxides are: dibenzoyl peroxide, dilauroyl peroxide and di-4-chlorobenzoyl peroxide.

Examples which may be mentioned of tertiary aromatic amines are N,N-dimethyl-p-toluidine, bis-(2-hydroxyethyl)-p-toluidine, bis(2-hydroxyethyl)-3,5-dimethylaniline and the N-methyl-N-(2-methyl-carbamoyloxypropyl)-3,5-dimethylaniline described in German Pat. No. A-2,759,239.

The concentrations of the peroxide and of the amine are advantageously chosen as 0.1 to 5% by weight, preferably 0.5 to 3% by weight, based on the monomer mixture. The peroxide- and amine-containing monomer mixtures are stored separately until used.

The monomers according to the invention can also be polymerized by irradiation with UV light or visible light (for example in the wavelength from 230 to 650 nm). Examples of suitable initiators for photoinitiated polymerization are benzil, benzil dimethyl ketal, benzoin monoalkyl ethers, benzophenone, p-methoxybenzophenone, fluorenone, thioxanthone, phenanthrenequinone and 2,3-bornanedione (camphorquinone), if appropriate in the presence of synergistically acting photoactivators, such as N,N-dimethylaminoethyl methacrylate, triethanolamine or 4-N,N-dimethylaminobenzenesulphonic acid bisallylamide.

The procedure of the photopolymerization process is described, for example, in German Pat. No. A-3,135,115.

In addition to the initiators described above, light stabilizers and polymerization inhibitors known per se for this use can be added to the (meth)-acrylic acid esters according to the invention.

The light stabilizer and the polymerization inhibitor are in each case in general employed in an amount of 0.01 to 0.50 part by weight per 100 parts by weight of the monomer mixture. The monomer mixtures can be employed as coating agents (dental lacquers) without the addition of fillers.

For use as dental filling compositions, fillers are in general added to the resulting monomer mixtures.

In order to be able to achieve a high volume fraction of the fillers, monomer mixtures which have a viscosity in the range from 60 to 10,000 mPa.s are particularly advantageous. Inorganic fillers can preferably be admixed to the monomer mixtures containing the compounds of the formula I according to the invention. Examples which may be mentioned are rock crystal, quartzite, cristobalite, quartz glass, highly disperse silicic acid, aluminum oxide and glass ceramics, for example glass ceramics containing lanthanum and zirconium (German Pat. No. A-2,347,591).

The inorganic fillers are preferably pretreated with an adhesion promoter to improve the bonding to the polymer matrix of the polymethacrylate. Adhesion promotion can be achieved, for example, by treatment with organo-silicon compounds (E. P. Plueddemann, Progress in Organic coatings, 11, 297 to 308 (1983)). 3-Methacryloyloxypropyltrimethoxysilane is preferably employed.

The fillers for the dental filling compositions according to the invention in general have an average particle diameter of 0.01 to 100 $\mu$m, preferably 0.05 to 50 $\mu$m and particularly preferably 0.05 to 5 $\mu$m. It may also be advantageous for several fillers which have different particle diameters and different degrees of silanization from one another to be employed side by side.

The filler content in the dental filling compositions is in general from 5 to 85% by weight, preferably 50 to 80% by weight.

To prepare the dental filling compositions, the components are processed using commercially available kneading machines.

The content of (meth)-acrylic acid derivatives according to the invention in the filling compositions is in general 10 to 75% by weight, preferably 15 to 60% by weight, based on the filling composition.

The (meth)-acrylic acid derivatives of triisocyanates according to the invention can also be used as components in the production of dentures.

The monomers according to the invention are here combined with the constituents which are usually employed and are known per se. The monomers are preferably employed as a mixture with alkyl methacrylates, such as methyl methacrylate. Bead polymers which are known per se can also additionally be added. Known inorganic and organic colored pigments and clouding agents can be added to adjust the tooth color. It is also possible to use stabilizers and light stabilizers.

The artificial teeth are produced by free radical polymerization of the dental compositions, with shaping.

Processing by either injection methods or embossing methods is possible, and is in general carried out in accordance with the customary production methods for teeth based on poly(methylmethacrylate), for example by polymerization by means of heat using polymerization initiators which are known per se, for example those based on peroxides and azo compounds, such as dibenzoyl peroxide, dilauroyl peroxide, cyclohexylpercarbonate, and azoisobutyrodinitrile. Mixtures of polymerization initiators with different dissociation temperatures are also particularly suitable.

The dental materials prepared from the (meth)acrylic acid esters according to the invention are distinguished by a high resistance towards mechanical stress and a high abrasion resistance.

EXAMPLE 1

Preparation of the adduct of 1,6,11-triisocyanatoundecane and glycerol dimethacrylate 27.9 g (0.1 mol) of 1,6,11-triisocyanato-undecane are dissolved in 100 ml of chloroform. 48 mg of 2,6-di-tert.-butyl-4-methyl-phenol and 100 mg of tin(II) octoate are added to this mixture. 68.4 g (0.3 mol) of glycerol dimethacrylate (isomer mixture of 1,3- and 1,2-bis-methacryloyloxy-propanol) are added dropwise at 30° C., with stirring. When the addition has ended, the mixture is stirred at 50° to 60° C. until the isocyanate groups have reacted completely.

The reaction is monitored by measurement of the IR spectra (isocyanate band at $\sim$2200 cm$^{-1}$).

The reaction mixture is cooled, filtered over Celite ® and freed from the solvent in vacuo.

EXAMPLE 2

Example 1 is repeated, with the modification that when the reaction has ended, triethylene glycol dimethacrylate (abbreviation: TEGDMA) is added to the reaction mixture and the solvent is then removed in vacuo. The TEGDMA content of the monomer mixture concentrated to constant weight is 40% by weight.

EXAMPLE 3

Preparation of a dental filling composition 198.3 parts by weight of a monomer mixture from Example 2 consisting of 60% by weight of the adduct of 1,6,11-triisocyanato-undecane and glycerol dimethacrylate and 40% by weight of triethylene glycol dimethacrylate, 0.4 part by weight of camphorquinone, 0.25 part by weight of benzil dimethyl ketal and 1.0 part by weight of 4-N,N-dimethylaminobenzenesulphonic acid bisallylamide are processed to a monomer solution, with exclusion of light. This solution hardens under visible light and/or UV light over an exposure time of 60 seconds to give a plastic which has a high mechanical stability.

To prepare a dental filling composition, 38 parts by weight of the abovementioned monomer solution and 62 parts by weight of a pyrogenic silicic acid (Aerosil OX 50) silanizid with 5% by weight of 3-methacryloyloxypropyl-trimethoxysilane are processed to a paste in a commercially available kneader at room temperature. A test specimen which has been produced from this paste and has been hardened in accordance with DIN 13922 using a commercially available dental light source has a very high flexural modulus, a very high flexural strength and an improved abrasion resistance.

What is claimed is:

1. A (meth)acrylic acid derivative of a triisocyanate of the formula

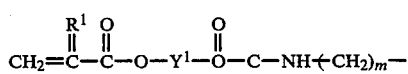

-continued

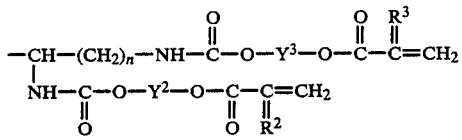

in which

R$^1$, R$^2$ and R$^3$ each independently denote hydrogen or methyl, m and n each independently represent a number from 2 to 6 and Y$^1$ to Y$^3$ each independently denote divalent straight-chain or branched aliphatic hydrocarbon radical which have 2 to 15 carbon atoms, said aliphatic hydrocarbon radicals can optionally contain 1 to 3 oxygen bridges and can optionally be substituted by 1 to 4 additional (meth)acryloyloxy radicals.

2. A (meth)acrylic acid derivative according to claim 1, wherein

R$^1$, R$^2$ and R$^3$ each independently denote hydrogen or methyl, the sum of m+n is 8 to 12, and Y$^1$ to Y$^3$ each independently denote divalent straight-chain or branched aliphatic hydrocarbon radicals which have 2 to 10 carbon atoms, said aliphatic hydrocarbon radicals can optionally contain 1 or 2 oxygen bridges and can optionally be substituted by 1 or 2 additional (meth)acryloyloxy radicals.

3. A (meth)acrylic acid derivative according to claim 1, wherein

R$^1$, R$^2$ and R$^3$ each independently denote hydrogen or or methyl, the sum of m+n is 9 to 11, and Y$^1$ to Y$^3$ each independently denote divalent straight-chain or branched aliphatic hydrocarbon radicals which have 2 to 10 carbon atoms, said aliphatic hydrocarbon radicals can optionally contain 1 or 2 oxygen bridges and can optionally be substituted by 1 or 2 additional (meth)acryloyloxy radicals.

4. A process for the preparation of a (meth)acrylic acid derivative of a triisocyanate according to claim 1, wherein a triisocyanate of the formula

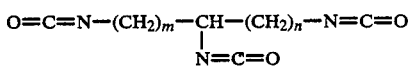

is reacted with an hydroxyalkyl (meth)acrylate of the formulae

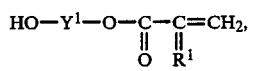

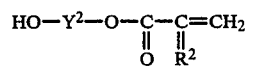

or

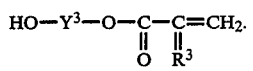

5. A process according to claim 4, wherein 0.9 to 1.1 mol of one or more of the hydroxyalkyl (meth) acrylates is employed for each isocyanate group of the triisocyanate.

6. A process according to claim 4, wherein the reaction is carried out in the temperature range from 20° to 100° C.

* * * * *